United States Patent
Tsukamoto

(10) Patent No.: US 8,634,516 B2
(45) Date of Patent: Jan. 21, 2014

(54) ENERGY SUBTRACTION IMAGING SYSTEM, X-RAY IMAGING APPARATUS, AND COMPUTER READABLE RECORDING MEDIUM

(76) Inventor: Hironori Tsukamoto, Lexington, MA (US)

(*) Notice: Subject to any disclaimer, the term of this patent is extended or adjusted under 35 U.S.C. 154(b) by 309 days.

(21) Appl. No.: 13/041,490

(22) Filed: Mar. 7, 2011

(65) Prior Publication Data

US 2011/0216883 A1 Sep. 8, 2011

Related U.S. Application Data

(60) Provisional application No. 61/311,361, filed on Mar. 7, 2010.

(51) Int. Cl.
*H05G 1/64* (2006.01)

(52) U.S. Cl.
USPC ........................................... 378/98.11

(58) Field of Classification Search
USPC .............................. 378/98.8, 98.11, 19, 98.12
See application file for complete search history.

(56) References Cited

U.S. PATENT DOCUMENTS

| | | | |
|---|---|---|---|
| 4,029,963 A | 6/1977 | Alvarez et al. | 378/5 |
| 6,843,598 B2 | 1/2005 | Minnigh et al. | 378/174 |
| 7,054,410 B2 | 5/2006 | Zentai et al. | 378/19 |
| 7,197,172 B1 | 3/2007 | Naidu et al. | 382/131 |
| 7,211,818 B2 | 5/2007 | Imai et al | 250/586 |
| 2002/0085671 A1* | 7/2002 | Sakaida | 378/98.11 |
| 2004/0228436 A1 | 11/2004 | Zentai et al. | 378/19 |
| 2007/0086639 A1 | 4/2007 | Sakaida | 382/132 |
| 2007/0116348 A1 | 5/2007 | Jabri | 382/132 |

* cited by examiner

*Primary Examiner* — Courtney Thomas

(57) ABSTRACT

An energy subtraction radiographic imaging system for providing energy subtraction images of an object includes an X-ray radiation source configured to generate X-rays having various energy levels transmitting through the object, a radiation imaging apparatus configured to operate in association with operation of the X-ray radiation source for receiving X-rays transmitted through the object, the radiation imaging apparatus including a first imaging device, a second imaging device and an attenuating element disposed between said first imaging device and the second imaging device, the attenuating element configured to substantially absorb the X-rays at lower energy levels and substantially allowing transmission of the X-rays at higher energy levels so that said second imaging device substantially receives the X-rays at higher energy levels.

18 Claims, 8 Drawing Sheets

ENERGY SUBTRACTION IMAGING SYSTEM, X-RAY IMAGING APPARATUS, AND COMPUTER READABLE RECORDING MEDIUM

RELATED APPLICATION DATA

This application claims the priority of U.S. Provisional Application No. 61/311,361, filed on Mar. 7, 2010, which is hereby incorporated in its entirety by reference.

BACKGROUND OF THE INVENTION

1. Field of the Invention

This invention relates generally to an energy subtraction imaging system, an X-ray imaging apparatus, and a computer readable recording medium, more specifically, an energy subtraction imaging system, an X-ray imaging apparatus and a computer readable recording medium having instructions executable by a computer to execute an energy subtraction radiographic imaging method.

2. Description of the Related Art

Radiation imaging apparatuses are widely used in the fields of medical diagnosis and security control system. In medical diagnosis, for example, energy subtraction radiography using the radiation imaging apparatuses can provide an X-ray image of boon selective images or tissue selective images.

The energy subtraction radiography (or dual energy projection radiography) has been investigated for decades, since the energy subtraction radiography provides a powerful tool for selectively imaging tumors or boons by subtracting two images obtained at different energy levels of X-ray. The image data are obtained from a lower energy radiograph and a higher energy radiograph taken from a body of a patient.

There are two types of energy subtraction radiography. One is based upon a single-exposure system and another is based upon a dual-exposure system.

In the single exposure system, a single exposure of X-rays is performed to the body of the patient to obtain a lower energy radiograph and a higher energy radiograph. Two phosphor plates and an energy filter are set in a cassette where the two phosphor plates are separated by the filter. To an X-ray source, one phosphor plate (a front side image plate) is located in front of the energy filter, and another phosphor plate (a rear side image plate) is located at the rear side of the energy filter. The front side image plate receives the whole energy beam of X-rays and forms a conventional X-ray image. The front side image plate and the energy filter are configured to select out lower energy photons of the X-rays so that the rear side image plate receives mostly higher energy photons of the X-rays and obtains a higher energy X-ray image.

A weighted subtraction is made between the conventional X-ray image and the higher energy X-ray image to produce a bone selective image, and a different weighted subtraction for the conventional X-ray image and the higher energy can produce a soft tissue selective image.

In dual exposure systems, first and second radiations of X-rays are sequentially performed to the body of a patient to obtain two radiographs. The two energies of the X-rays for the first and second radiations are produced by an X-ray tube biased at 60 kilovolts peak (kVp) and 120 kilovolts peak (kVp), respectively. After the first exposure, the second exposure is performed about 0.2 second after the first exposure. This delay may cause misregistration artifacts on the subtracted images because of cardiac, respiratory, bowel and patent motion.

Maintaining multiple sets of X-ray sources may increase the operating and overhead costs for medical diagnostic facility. It may also affect the efficiency of the facility by increasing the idle time of the apparatuses. Accordingly, it would be advantageous to have a single exposure energy subtraction imaging system that is capable of forming images using X-rays at different energy levels. It would be desirable for the apparatus to be simple, reliable, and capable of being used with an existing X-ray imaging system. It would be advantageous when the single exposure energy subtraction imaging system improves its image quality of signal-to-noise ratio for the real time X-ray imaging for the diagnosis.

SUMMARY OF THE INVENTION

This invention takes into consideration the issues above. One of the objects of this invention may be to provide an energy subtraction imaging system, an X-ray imaging apparatus and a computer readable recording medium having instructions executable by a computer to execute an energy subtraction radiographic imaging method.

Accordingly, embodiments of the present invention may provide a novel and useful solution for one or more of the problems discussed above.

More specifically, the embodiments of the present invention may provide an energy subtraction imaging system including an X-ray radiation source configured to generate X-rays having various energy levels including lower energy levels and higher energy levels transmitting through the object; a radiation imaging apparatus configured to operate in association with operation of the X-ray radiation source for receiving X-rays transmitted through the object, the radiation imaging apparatus including a first imaging device, a second imaging device and an attenuating element disposed between said first imaging device and said second imaging device, the attenuating element configured to substantially absorb the X-rays at lower energy levels and substantially allowing transmission of the X-rays at higher energy levels so that said second imaging device substantially receives the X-rays at higher energy levels, said first imaging device configured to include a first pixel array capable of generating first electric signals by receiving the X-rays transmitted through the object and include a first circuitry capable of acquiring said first electric signals from said first pixel array and forming first digital image data of the object using said first electric signals for outputting said first digital image data, and a first storage device for storing said first digital image data of the object output from the first circuitry, said second imaging device configured to include a second pixel array capable of generating second electric signals by receiving the X-rays at higher energy levels transmitted through the attenuating element and include a second circuitry capable of acquiring said second electric signals from the second pixel array and forming second digital image data of the object using said second electric signals output from the second circuitry, and a second storage device for storing said second digital image data of the object output from the second circuitry; and an image processing device configured to acquire said first and second digital image data output respectively from said first and second imaging devices for providing energy subtraction radiographic images of the object using said first and second digital image data.

In another embodiment, the embodiments of the present invention may provide a radiation imaging apparatus for providing subtraction images of an object including a first imaging device, a second imaging device and an attenuating element disposed between said first imaging device and said second imaging device, said first and second imaging device configured to receive X-rays at various energy levels including higher energy levels and lower energy levels, the attenuating element configured to substantially absorb the X-rays at the lower energy levels and substantially allowing transmission of the X-rays at the higher energy levels so that said second imaging device receives the X-rays at the higher energy levels, said first imaging device configured to include a first pixel array capable of generating first electric signals by receiving the X-rays transmitted through the object and include a first circuitry capable of acquiring and outputting said first electric signals, said second imaging device configured to include a second pixel array capable of generating second electric signals by receiving the X-rays transmitted through the attenuating element and include a second circuitry capable of acquiring and outputting said second electric signals; and an image processing device configured to acquire said first and second electric signals output from said first and second imaging devices for processing said first and second electric signals for providing subtraction radiographic images; wherein said first and second imaging devices operate in association with one another for processing characteristics of the X-rays.

In another embodiment, the embodiments of the present invention may provide a computer readable recording medium having instructions executable by a computer to execute an energy subtraction radiographic imaging method including the steps of receiving X-rays at various energy levels including higher energy levels and lower energy levels using a first imaging device capable of converting signals caused by the X-rays into a first digital image dataset; receiving the X-rays using an attenuating element capable of substantially absorbing the X-rays at lower energy levels and substantially transmitting the X-rays at higher energy levels; receiving the X-rays at higher levels using a second imaging device capable of converting signals caused by the X-rays at higher energy levels into a second digital image dataset; and forming an energy subtraction image dataset using said first digital image dataset and second image dataset.

DETAILED DESCRIPTION OF THE PREFERRED EMBODIMENTS

Figure 1:
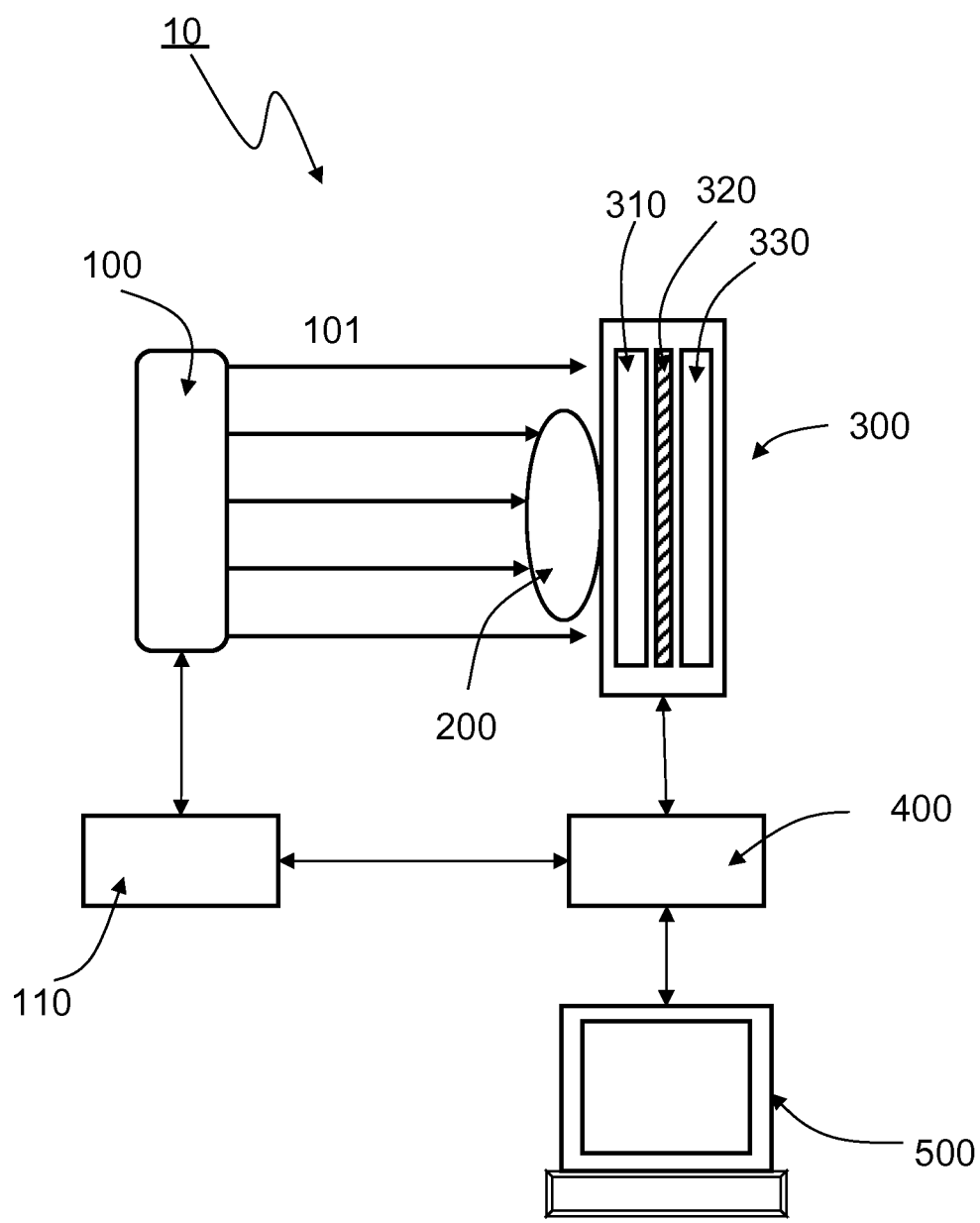
FIG. 1 illustrates an example of an energy subtraction imaging system 10.

Various embodiments of the present invention are described hereafter with reference to the figures. It would be noted that the figures are not drawn to scale and elements of similar structures or functions are represented by like reference numerals throughout the figures. It should be also noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

FIG. 1 shows an illustration of an energy subtraction imaging system 10 in accordance with an embodiment of the present invention. The energy subtraction imaging system 10 includes an X-ray source 100 including a signal processor (not shown) for operating a power supplier for generating X-rays 101 having various energy levels, an X-ray source control unit 110 for managing signals of the operation of the X-ray source 100, an X-ray imaging apparatus 300 for acquiring X-ray projection images of an object 200, a data processing apparatus (or image processing device) 400 for operating the X-ray imaging apparatus 300 to form energy subtraction X-ray projection images of the object 200, and a computer unit 500 for displaying and analyzing the X-ray projection images. The X-ray imaging apparatus 300 includes an imaging device 310, an attenuating element 320 and an imaging device 330 for acquiring X-ray images of the X-rays 101 at lower energy levels and higher energy levels. Further, the X-ray imaging apparatus 300 may include the data processing apparatus 400. Further, the data processing apparatus 400 may include a media unit for reading and recording data, and executing a computer program recorded in a recording medium. The object 200 is positioned between the X-ray source 100 and the X-ray imaging apparatus 300 so that the X-ray imaging apparatus 300 receives the X-rays 101 after the X-rays 101 transmits the object 200. Then, X-ray projection images of the object 200 are detected by the X-ray imaging apparatus 300.

The computer unit 500 also includes a medium unit for reading and executing a computer program. The X-ray source control unit 110 is coupled to the X-ray source 100 and the data processing apparatus 400 via electrical wires, optical fiber connections, radio wireless communication system or optical wireless communication system for their operation control. The data processing apparatus 400 is coupled to the X-ray imaging apparatus 300 and the computer unit 500 via electrical wiring, optical fiber connections, wireless communication system, or optical wireless communication system for their operation control.

The nature of the object 200 depends on the application of the energy subtraction imaging system 10. For example, in one application according to the present invention, the energy subtraction imaging system 10 may include medical diagnostic equipment and the object 200 is a body of a patient. In another application, the energy subtraction imaging system 10 is biological measuring equipment and the object 200 is an animal or plant. In another application, the energy subtraction imaging system 10 is security or custom inspection equipment and the object 200 is a luggage or baggage to be inspected. In another application, the energy subtraction imaging system 10 is structure equipment and the object 200 is a machine or part of a machine to be inspected.

The X-ray source control unit 110 is connected to the data processing unit 400 via electrical wiring, radio wireless network, optical fibers or optical wireless network. The data processing apparatus 400 operates in association with the X-ray source control unit 110 and the X-ray imaging apparatus 300 for synchronizing operations of the X-ray source 100 and the X-ray imaging apparatus 300 by signal communications.

Figure 2:
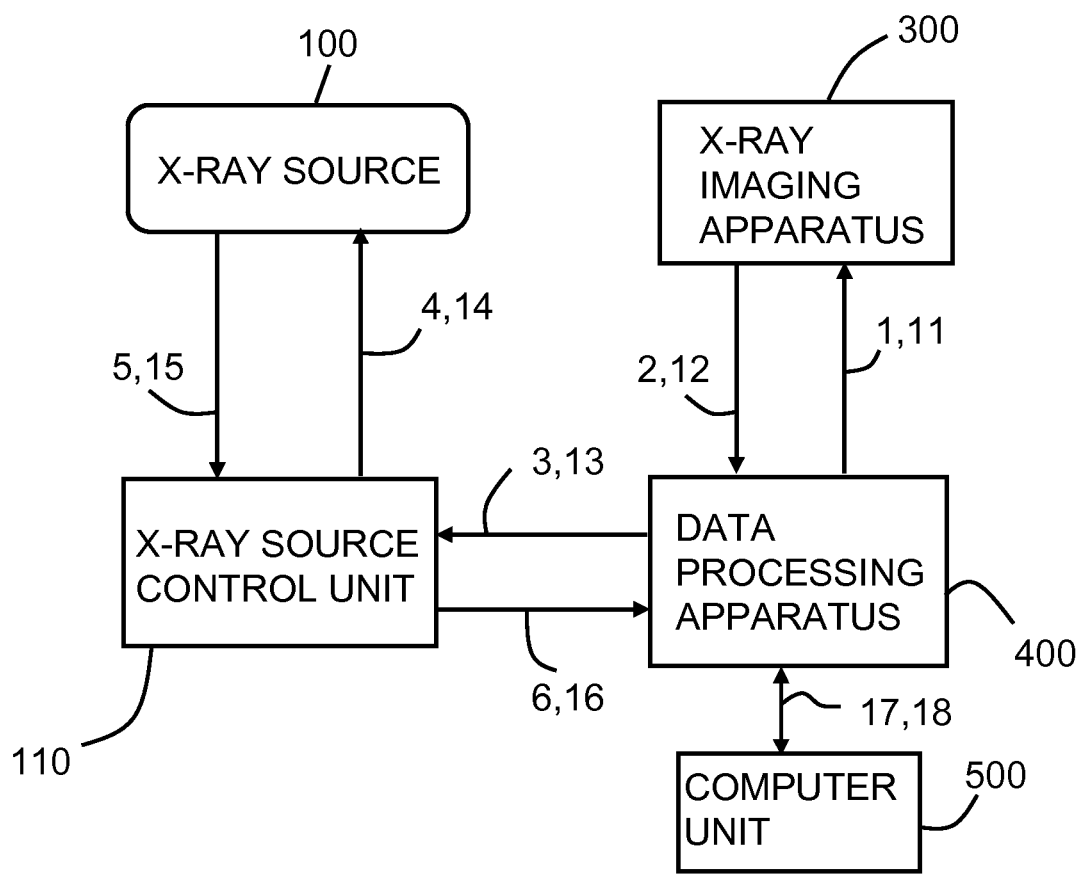
FIG. 2 illustrates a block diagram illustrating an example of data communication of the energy subtraction imaging system 10.

FIG. 2 shows a block diagram illustrating an example of data communication of the energy subtraction imaging system 10. In the energy subtraction imaging system 10 according to an embodiment of the present invention, operation control between the X-ray source 100, the X-ray source control unit 110, the data processing apparatus 400, the X-ray imaging apparatus 300 and the computer unit 500 may be performed based on data communication via electrical wiring, optical fiber connections, wireless communication system, or optical wireless communication system for their operation control. The operation of the data processing apparatus 400 may be performed by an operator person using the computer unit 500.

For taking an X-ray projection image of the object 200, for example, the data processing apparatus 400 transmits a first process control signal 1 indicating a turn-on signal to the X-ray imaging apparatus 300. After receiving the first process control signal 1, the X-ray imaging apparatus 300 prepares an operation of imaging for detecting (or imaging) the X-rays 101 and returns a first imaging operation signal 2 to the data processing apparatus 400 for informing that the operation of imaging is ready. After transmitting the first imaging operation signal 2 to the data processing apparatus 400, the X-ray imaging apparatus 300 starts detecting the X-rays 101 in a predetermined time period, which is approximately in 0.01 second, and simultaneously, the X-ray imaging apparatus starts storing image data of the X-rays 101 detected respectively by the imaging devices 310 and 320 into respective storage devices of the imaging devices 310 and 320.

While detecting the X-rays 101 using the imaging devices 310 and 320 shown in FIG. 1, the data processing apparatus (image processing device) 400 and the X-ray imaging apparatus 300 can acquire the image data respectively detected by the imaging devices 310 and 320 for performing real time data processing. The data processing may perform data communication with the computer unit 500 for providing real time imaging of projection images of the X-rays 101 with a display monitor. The display monitor may be positioned separated from the computer of the computer unit 500.

When receiving the first imaging operation signal 2 from the X-ray imaging apparatus 300, the data processing apparatus 400 transmits a first process control signal 3 indicating a predetermined operation time period to the X-ray source control unit 110 for operating the X-ray source 100 for the predetermined operation time period to emit X-rays 101. The first process control signal 3 includes a signal informing a predetermined operation period of the X-ray source 100. In response to the first process control signal 3 from the data processing apparatus 400, the X-ray source control unit 110 transmits a first source control signal 4 to the X-ray source 100. The first source control signal 4 includes the signal informing the predetermined operation period of the X-ray source 100.

When the X-ray source control unit 110 transmits the first source control signal 4 indicating a turn-on signal to the X-ray source 100, the X-ray source 100 starts emitting the X-rays 101 in a first predetermined time period in response to the first source control signal 4, and simultaneously, the X-ray source 100 returns a first source return signal 5 to the X-ray source control unit 110 for informing that the X-ray source 100 emits the X-rays 101. The first predetermined time period may be shorter than 1 second, more preferably, the first predetermined time may be approximately 0.01 second or shorter.

In response to the first return signal 5 from the X-ray source 100, the X-ray source control unit 110 transmits a first process return signal 6 to the image data processing apparatus 400. Then in response to the first process return signal 6, the data processing apparatus 400 starts reading and storing X-ray imaging data detected by the X-ray imaging apparatus 300.

When the operation time of the X-ray source 100 has passed the predetermined operation time period, the X-ray source control unit 110 transmits a second source control signal 14 indicating a turn-off signal to the X-ray source 100, and the X-ray source 100 stops emitting the X-rays 101 in a second predetermined time period in response to the second source control signal 14, and simultaneously, the X-ray source 100 returns a second return signal 15 to the X-ray source control unit 110 for informing that the X-ray source 100 stops emitting the X-rays 101. The second predetermined time period may be shorter than 0.1 second, more preferably, the second predetermined time period may be approximately 0.01 second or shorter than 0.01 second. The X-ray source control unit 110 transmits a second process return signal 16 to the data processing apparatus 400 after receiving the second return signal 15 from the X-ray source 100, where the second process return signal 16 indicates that the X-ray source stops emitting the X-rays 101. In response to the second process return signal 16, the data processing apparatus 400 transmits a second process control signal 11 indicating turn-off signal to the X-ray imaging apparatus 300. In response to receiving the second process control signal 11, the X-ray imaging apparatus 300 stops its operation. After stopping the operation of imaging, the X-ray imaging apparatus 300 transmits a second imaging operation signal 12 to the data processing apparatus 400 for informing that the operation of imaging is stopped.

Although a simplified signal communication of the energy subtraction imaging system 10 is described the above, the energy subtraction imaging system 10 may include any signal communication between the X-ray source 101, the X-ray source control unit 110, the data processing apparatus 400, the X-ray imaging apparatus 300 and the computer unit 500. Further, the energy subtraction imaging system 10 may include an interlock safety system which can safely shut down the X-ray source for stopping emission of the X-rays 101 with synchronizing the whole system in the energy subtraction imaging system 10.

In accordance with an embodiment of the present invention, an imaging process of the imaging devices 310 and 330 included in the X-ray imaging apparatus 300 will be described with reference to FIG. 3A, FIG. 3B and FIGS. 4A and 4B.

The X-ray imaging apparatus 300 includes a process unit (not shown) for performing communication with peripheral apparatuses such as the data processing apparatus 400 shown in FIG. 2. As the imaging device 310 and the imaging device 330 have similar structures, identical notations are used for explaining the imaging devices 310 and 330.

Figure 3A:
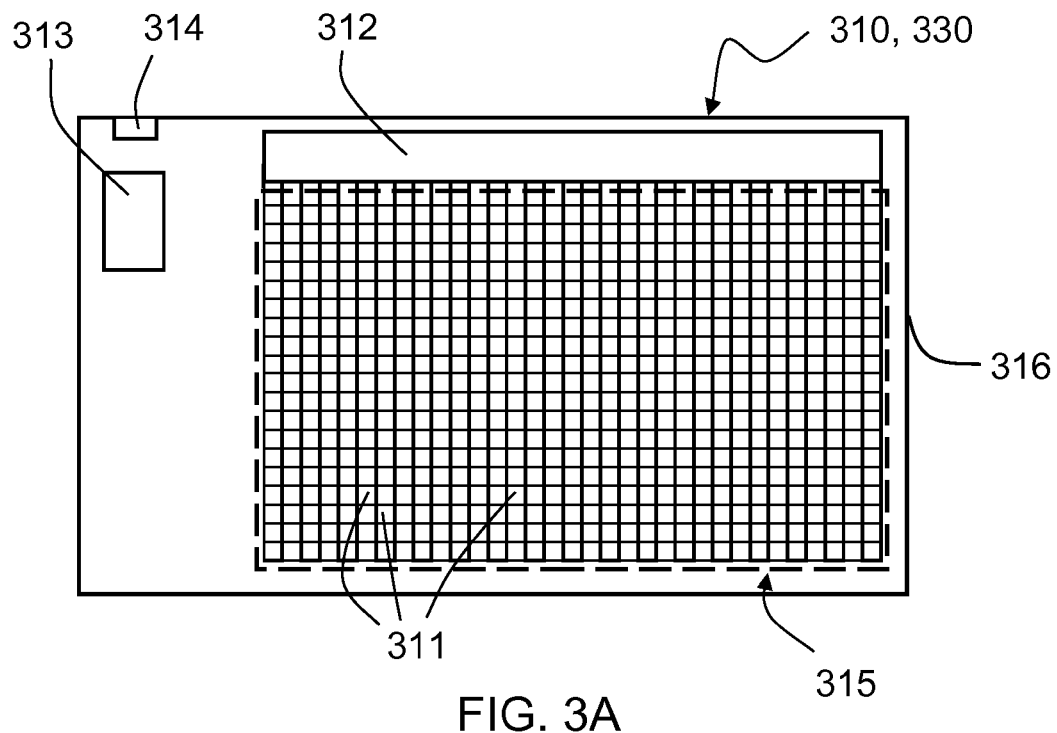
FIG. 3A illustrates an embodiment of the imaging device 310 and 330.

FIG. 3A shows an illustration of an example of the imaging devices 310 and 330. Each of the imaging devices 310 and 330 includes an access circuit 312, a storage device 313, a data communication port 314, a detective pixel array 315 formed by plural detective pixels 311 and a device substrate 316. The access circuit 312, the storage device 313, the data communication port 314 and the detective pixel array 315 are secured on the device substrate 316.

Figure 4A:
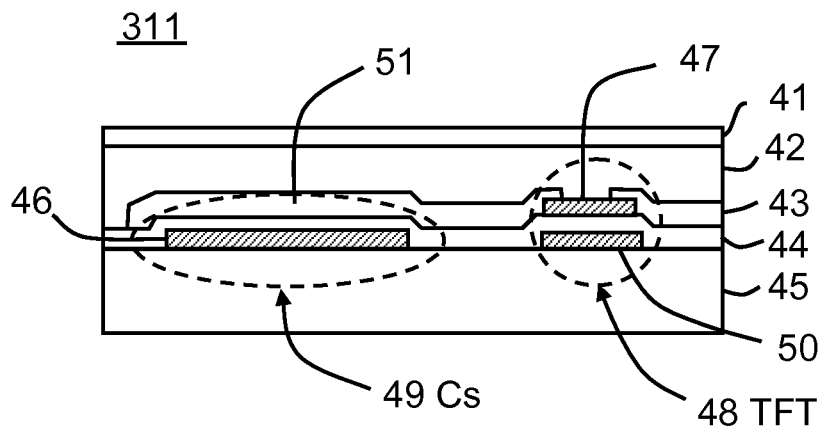
FIG. 4A illustrates an embodiment of a cross section of the detective pixel 311.
Figure 4B:
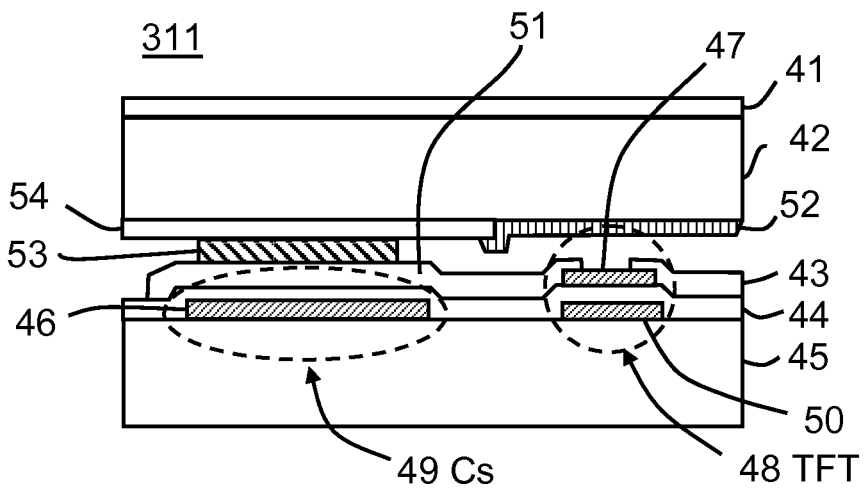
FIG. 4B illustrates another embodiment of a cross section of the detective pixel 311.

Each of the detective pixels 311 includes a signal generating layer 42 in FIGS. 4A and 4B, a storage capacitor and a switching element such as a thin-film-transistor (TFT) or a diode switch. The structures of the detective pixel 311 will be described later. The procedures of accessing the detective pixel array 315 with the pixel access circuit 312 for reading the electric signals from the detective pixel array 315 is known to those skilled in the art.

When the detective pixels 311 receive the X-rays 101, each of the detective pixels 311 generates electric charges relevant to received intensity of the X-rays 101 and stores the electric charges to the storage capacitor. The detective pixel array 315 is coupled to the access circuit 312. When the access circuit 312 accesses one of detective pixels 311 of the detective pixel array 315, the detective pixel 311 of the detective pixel array 315 transfers the electric charges stored in the storage capacitor of the detective pixel 315 to the access circuit 312. The access circuit 312 receives the electric charges of the detective pixel 315 as an analog signal. The access circuit 312 includes an analog-digital (A/D) converter (not shown) so that the analog signal of the detective pixel 315 can be converted to digital image data. After converting the analog signal to the digital image data, the access circuit 312 stores the digital image data to the storage device 313 with information of a corresponding pixel address of the detective pixel 311 on the pixel array 315.

The imaging process described above is continued for the whole detective pixels 311 of the pixel array 315 during a predetermined time period as a single frame image formation. The single frame image formation is continuously performed with interval between the predetermined time periods for another frame image formation.

As described above, the digital image data of the X-rays 101 are stored to the storage device 313. The image data of one of the detective pixels 311 may be gray scales relevant to intensity of the X-rays 101 received by the one of the detective pixel 311. Since the X-rays 101 transmits the object 200, the digital image data of the X-rays 101 received by the imaging devices 310 and 330 represent X-ray projection images of the object 200. The digital image data of the X-rays 101 may indicate gray scales relevant to intensity of the X-rays 101 representing X-ray contrast images of the object 200.

As described above, the access circuit 312 is coupled to the storage device 313, so that the access circuit 312 can transmit and store the digital image data of the X-rays 101 detected by the detective pixel array 315 to the storage device 313. In this manner, the access circuit 312 accesses the detective pixel array 315 and reads electric signals out from the detective pixel array 315. Further, the imaging devices 310 and 330 are configured to expose only area of the pixel array 315 to the X-rays 101 for protecting the access circuit 312, the storage device 313, the data communication port 314 and other electrode area of each of the imaging devices 310 and 330 from the exposure to the X-rays 101.

Figure 3B:
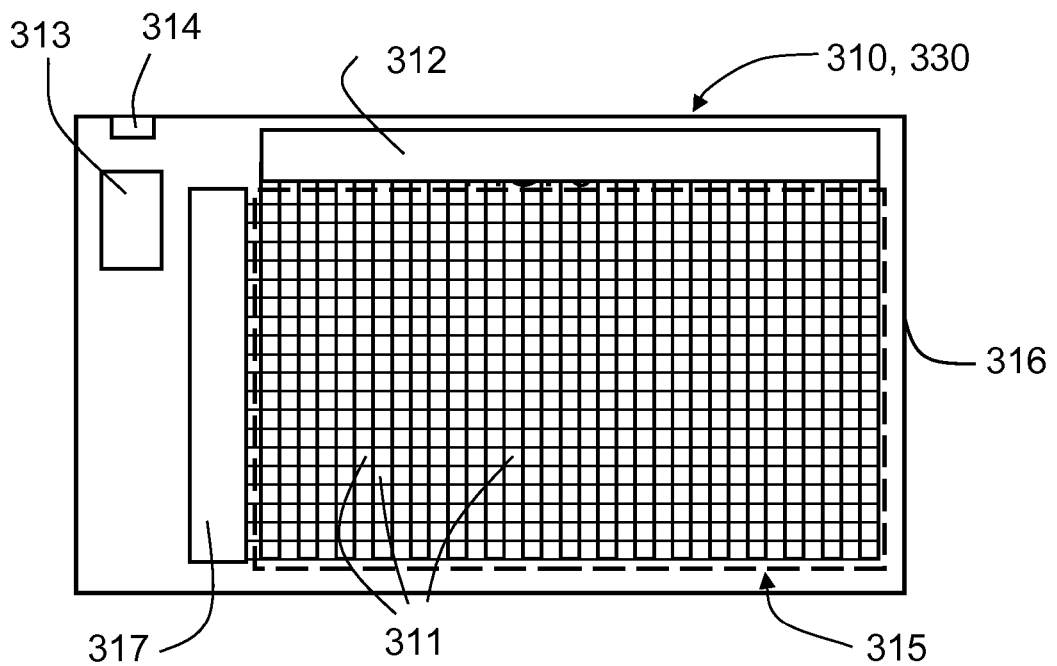
FIG. 3B illustrates another embodiment of the imaging device 310 and 330.

Alternatively, each of the imaging devices 310 and 330 may include another pixel access circuit 317 coupled to the detective pixel array 315 as shown in FIG. 3B. As most parts of the imaging devices 310 and 330 are similar to those of the imaging devices 310 and 330 in FIG. 3A except another pixel access circuit 317, identical notations are used except the another pixel access circuit 317. In this case, one of the access circuits 312 and 317 is configured to select a row of the pixel array 315 and another one of the access circuits 312 and 317 is configured to select a column to access one of the detective pixels of the pixel array 315 for reading image data out from the one of the detective pixels 311. The imaging devices 310 and 330 are configured to expose only area of the pixel array 315 to the X-rays 101 for protecting the access circuits 312 and 317, the storage device 313, the data communication port 314 and other electrode area of each of the imaging devices 310 and 330 from the exposure to the X-rays 101.

The storage device 313 coupled to the data communication part 314 that is connected to the process unit (not shown) included in the X-ray imaging apparatus 300 via electrical wiring, optical fiber connections, wireless communication system, or optical wireless communication system for data communication.

As way of an explanation in accordance with an embodiment of the present invention, a cross section of the detective pixel 311 is described with reference to FIG. 4A.

The detective pixel 311 may be a direct conversion type detector. The detective pixel 311 includes the signal generating layer 42, an electrode 41, a switching element 48, a storage capacitor 49 and a device substrate 45. The signal generating layer 42 is secured between the electrode 41 and underlying the storage capacitor 49 and the switching element 48. The switching element 48 may be a thin film transistor (TFT) 48 coupled to the electrode 43 and the storage capacitor 49. Alternatively, a diode switching element may be used as the switching element 48 instead of the thin film transistor 48. As an example for explanations of the present embodiment, a thin film transistor (TFT) 48 is used in the detective pixel 311. A signal line is omitted in figures. The structure of the TFT 48 and the operation of the TFT 48 and the storage capacitor 49 are understood by those skilled in the art.

The TFT 48 includes a signal electrode 43, the insulating film 44, a channel layer 47 and a gate electrode 50. The storage capacitor 49 includes a capacitor electrode 51 coupled to one of ends of the channel layer 47 of the TFT 48, the insulating film 44 and a capacitor film 46 formed from such as poly-silicon, amorphous silicon, single crystal silicon, or other electrode materials. The TFT 48 and the storage capacitor 49 are secured on the device substrate 45. The device substrate 45 is formed from insulating materials such as a glass, polyimide films or the like.

When the X-rays 101 penetrate into the signal generating layer 42, electron-hole pairs are generated in the signal generating layer 42, and the electrons or holes are collected to one of the electrode 41 and the capacitor electrode 51. The collection of the electrons or holes is dependent on an electric field applied to the electrode 41 and the capacitor electrode 51. For example, when the electrode 41 is biased with positive voltage while the capacitor electrode 51 is biased with negative voltage, the electrons are collected towards the electrode 41 and the holes are collected towards the capacitor electrode 51. The electric field applied between the electrode 41 and the capacitor electrode 51 may be between 0.1 V/μm and 10 V/μm. The holes collected by the capacitor electrode 51 are used as pixel charges that are stored to the storage capacitor (Cs) 49.

The signal generating layer 42 may be an amorphous selenium (a-Se) layer, a cadmium telluride (CdTe) layer, a cadmium zinc telluride (CdZnTe), amorphous silicon (a-Si) layer, a poly silicon (poly-Si) layer, a gallium arsenide (GaAs) layer, a gallium selenium (GaSe) layer, a gallium antimonide (GaSb) layer, an indium antimonide (InSb) layer, a germanium (Ge) layer, an indium cadmium telluride (InCdTe) layer or an indium arsenide (InAs) layer, a mercuric iodide ($HgI_2$) layer, a lead iodide ($PbI_2$), a bismuth iodide ($BiI_3$), a cesium iodide (CsI), or equivalents thereof. The number of electrons or holes collected by the electrode 43 depends upon a dose of the X-rays 101. When the dose of the X-rays 101 received by the charge generation layer 42 is increased, the number of the electron-hole pairs generated in the charge generation layer 42 increases. When the dose of the X-rays 101 is decreased, the number of the electron-hole pairs generated in the charge generation layer 42 decreased.

Alternatively, another structure may be used for the detective pixel 311 as shown in FIG. 4B. Another type detective pixel 311 has similar structure those of the detective pixel 311 of FIG. 4A. The detective pixel 311 of FIG. 4B further includes a passivation film 52, a connecting electrode 53 and a bottom electrode 54.

When the X-rays 101 penetrate into the signal generating layer 42, electron-hole pairs are generated in the signal generating layer 42, and the electrons or holes are collected to one of the electrode 41 and the capacitor electrode 51. The collection of the electrons or holes is dependent on an electric field applied to the electrode 41 and the bottom electrode 54. For example, when the electrode 41 is biased with positive voltage while the bottom electrode 54 is biased with negative voltage, the electrons are collected towards the electrode 41 and the holes are collected towards the bottom electrode 54. The electric field applied between the electrode 41 and the bottom electrode 54 may be between 0.1 V/μm and 10 V/μm. The connecting electrode 53 is formed by a conductor material so that the charges collected by the bottom electrode 54 can transfer to the capacitor electrode 51. An electric potential of the capacitor electrode 51 may be equivalent to that of the bottom electrode 54 or slightly smaller than the electric potential of the bottom electrode 54 so that the holes are used as pixel charges that are stored to the storage capacitor (Cs) 49.

The signal generating layer 42 may be an amorphous selenium (a-Se) layer, a cadmium telluride (CdTe) layer, a cadmium zinc telluride (CdZnTe), amorphous silicon (a-Si) layer, a poly silicon (poly-Si) layer, a gallium arsenide (GaAs) layer, a gallium selenium (GaSe) layer, a gallium antimonide (GaSb) layer, an indium antimonide (InSb) layer, a germanium (Ge) layer, an indium cadmium telluride (InCdTe) layer or an indium arsenide (InAs) layer, a mercuric iodide ($HgI_2$) layer, a lead iodide ($PbI_2$), a bismuth iodide ($BiI_3$), a cesium iodide (CsI), or equivalents thereof. The number of electrons or holes collected by the electrode 43 depends upon a dose of the X-rays 101. When the dose of the X-rays 101 received by the signal generating layer 42 is increased, the number of the electron-hole pairs generated in the signal generating layer 42 increases. When the dose of the X-rays 101 is decreased, the number of the electron-hole pairs generated in the signal generating layer 42 decreased.

The signal generating layer 42 may be deposited by physical vapor deposition (PVD) or particle in binder process. In another embodiment, the signal generating layer 42 may be formed by wafer bonding process. Alternatively, if the signal generating layer 42 is deposited on a separate substrate such as CdZnTe. Alternatively, the signal generating layer 42 may be secured to the electrodes 41 and 43 and 51. Other methods known in the art may also be applied to secure the signal generating layer 42 to the electrodes 41 and 51.

In accordance with an embodiment of the present invention, the access circuit 312 accesses the pixel array 315 to read an image dataset for obtaining a single frame image dataset.

When the access circuit 312 accessed the TFT 48 of the detective pixel 311, the pixel charge stored with the storage capacitor 46 is transferred to the access circuit 312. The access circuit 312 receives the pixel charge from the storage capacitor 49 through the channel layer 47 of the TFT 58 and converts the pixel charge into digital image data with a preamplifier (not shown) and an A/D converter (not shown) included in the access circuit 312. The digital image data indicate X-ray image contrast of a pixel. The digital image data of the pixel charge is transmitted to the storage device 313. The access circuit 312 continues to access the pixel array 315 until the whole pixel charges of the pixel array 315 are collected and converted respectively into the digital image data. The whole digital image data of the pixel array 315 are stored into the storage device 313 as a frame image dataset.

Figure 5:
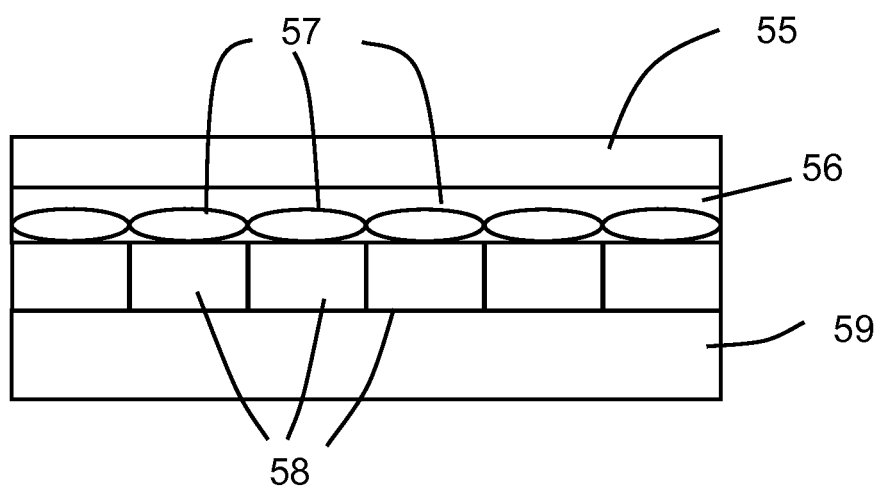
FIG. 5 illustrates another embodiment of a cross section of the detective pixel 311 formed by charge coupled devices.

Alternatively, the pixel array 315 may be formed by charge coupled devices (CCDs). The operation of the CCDs and data transfer circuit formed with the CCDs are know to those skilled in the art. Therefore, the detail explanation of operation and structure of the CCDs are omitted. FIG. 5 shows an example illustrating the pixel array 315 formed by the CCDs. The pixel array 315 includes a scintillating layer 55, on-chip micro-lenses 57, CCDs 58 and a substrate 59. The scintillating layer 55 is formed over the on-chip micro-lenses 57 with a predetermined separation. Each of the on-chip micro-lenses 57 is secured on each of the CCDs 58. The scintillating layer 55 and CCDs 58 are formed on the substrate 59. The substrate 59 may be formed by a silicon substrate, glass substrate, a plastic substrate, an epoxy resin substrate or the like.

When receiving the X-rays 101 on a spot of the scintillating layer 55, the scintillating layer 55 of the spot emits light. The light is substantially collimated by one of the on-chip micro-lenses 58 which positions closest to the spot and the collimated light is transmit to its underlying CCD 58. The CCD 58 generates electric signals and transfers the electric signals to peripheral circuit (not shown) of the CCDs 58. The transferred electric signals are amplified at the peripheral circuit of the CCDs 58 and converted to digital image data by an A/D converter (not shown) and stored into the storage device 313.

As shown in FIG. 1, the attenuating element 320 is disposed between the imaging device 310 and the imaging device 330. The attenuating element 320 plays a role of an X-ray energy selecting filter. The X-rays 101 includes a broad energy spectrum between approximately 10 kilo-electron-volt (keV) and approximately 150 kilo-electron-volt (keV). The attenuating element 320 is configured to substantially absorb the X-rays 101 at lower energy levels. This makes it possible for the imaging device 330 to substantially absorb the X-rays 101 at higher energy levels. As a result, the imaging device 330 dominantly absorbs the X-rays 101 at higher energy levels, while the imaging device 310 dominantly absorbs the X-rays 101 at lower energy levels. For example, the attenuating element 320 may be configured to absorb X-rays at an energy level of approximately 50 keV or less than 50 keV. The attenuating element 320 is also configured to substantially transmit higher energy levels of the X-rays 101. The attenuating element 320 may be configured to maximize transmitting the X-rays 101 at energy levels higher than 50 keV. The attenuating element 320 may be made from a material such as copper (Cu), molybdenum (Mo), cadmium (Cd), tin (Sn), tellurium (Te), indium (In), silicon (Si), gallium arsenide (GaAs), gallium nitride (GaN), indium arsenide (InAs), indium antimonide (InSb), selenium (Se) or a material made from combination of those materials. Thicker attenuating element 320 causes scattering of the X-rays. This may degrade the resolution of X-ray images. For example, Mo may be used as a material of the attenuating element. A thickness of Mo may be between 0.01 millimeter and 0.5 millimeter. More specifically, the thickness of Mo may be approximately 0.1 millimeter. In another example, copper having a thickness of approximately between 0.1 millimeter and 1.2 millimeter may be used. More specifically, the thickness of Cu may be approximately 1.0 millimeter. An appropriate thickness of Cu should be chosen depending on applications, since if the thickness of Cu is too thick, the intensity of X-rays impinging on the imaging device 330 is reduced. As a result, an image quality of X-rays being detected with the imaging device 330 might be poor. Therefore, the thickness of the attenuating element should be minimized.

The attenuating element 320 is made from a predetermined material and having a thickness for substantially attenuating a first predetermined energy component of the X-rays 101 and for being substantially transparent to a predetermined second energy component of the X-rays 101. The attenuating element is capable of shielding light. The attenuating element 320 may be made from a material such as Cu, Mo, Cd, Sn, and semiconductor materials such as silicon, germanium, GaAs, GaN, SiC, InSb, Se, or combination of those materials. As an example, the attenuating element 320 may be a copper plate having a thickness of approximately 1 millimeter (mm). As amount of the X-rays having lower energy components of the X-rays 101 being attenuated by the copper plate increases with increase of the thickness of the copper plate, a preferable thickness of the copper plate is chosen for obtaining appropriate transmission of the rest of the X-rays 101.

Figure 6:
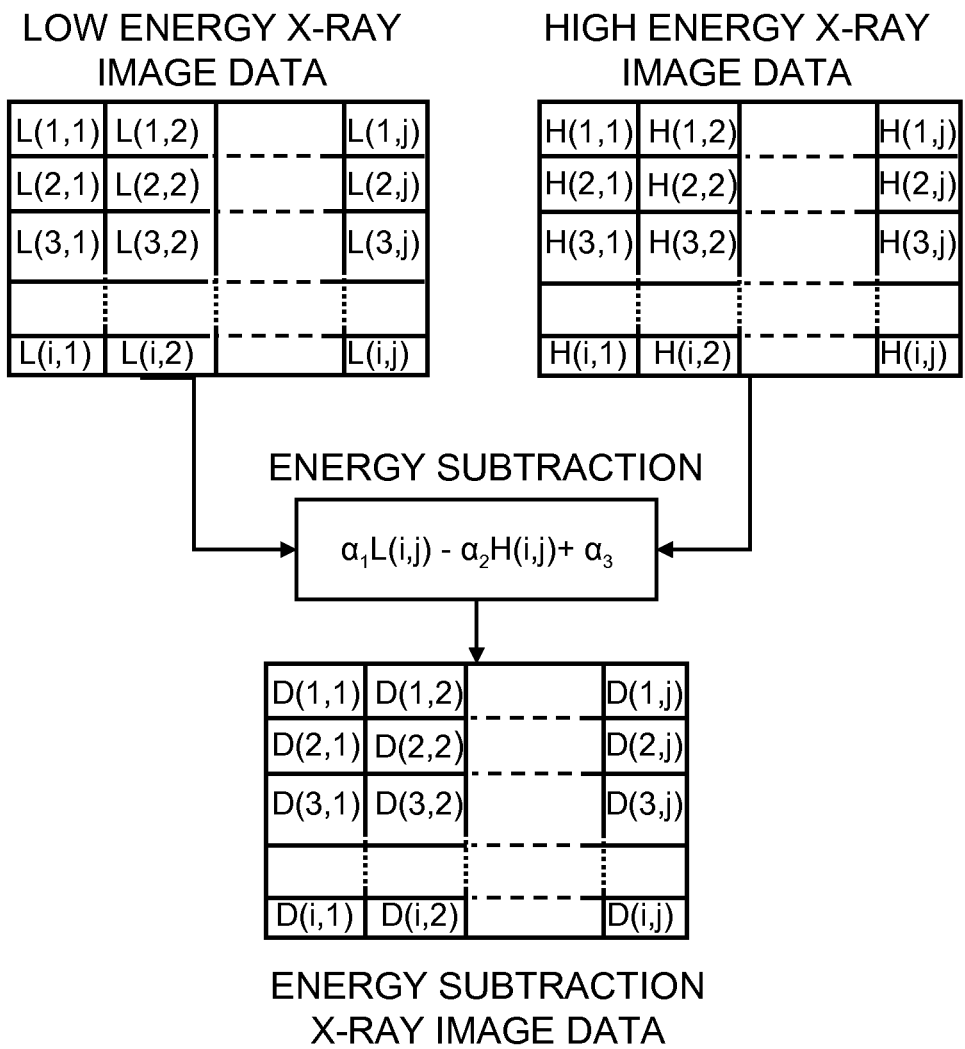
FIG. 6 illustrates an embodiment of dataset structures for producing an energy subtraction X-ray image dataset.

FIG. 6 shows an example of dataset structures for producing an energy subtraction X-ray image dataset.

When receiving the X-rays 101, the imaging device 310 produces a lower energy image dataset L(i,j) having an array structure L(i,j), where i and j are integers, i>0 and j>0. The image dataset L(i,j) are digital data stored in the storage device 313 of the imaging device 310. The image dataset L(i,j) indicates that there are numbers of i-th row and j-th column in the L(i,j). Data arrangement of the dataset L(i,j) corresponds to the pixel arrangement of the pixel array 315 so that an X-ray image formed by the imaging device 310 is matched to the data arrangement of the dataset L(i, j). In the same manner, the imaging device 330 produces a higher energy image data set H(i,j) having an array structure H(i,j), where i and j are integers, i>0 and j>0. The image dataset H(i, j) are digital data stored in the storage device 313 of the imaging device 330. The image dataset H(i,j) indicates that there are numbers of i-th row and j-th column in the H(i,j). Data arrangement of the image data H(i,j) corresponds to the pixel arrangement of the pixel array 315 of the imaging device 330 so that an X-ray image formed by the imaging device 330 is matched with the data arrangement of the image dataset H(i,j).

An example of energy subtraction X-ray imaging will be described in the following. As described above, the imaging device 310 dominantly absorbs the X-rays 101 at lower energy levels, and the imaging device 330 dominantly absorbs the X-rays 101 at higher energy levels. Therefore, the image data set L(i,j) produced by the imaging device 310 is relevant to lower energy X-ray projection image (or lower energy image), and the image data set H(i,j) produced by the imagining device 330 is relevant to higher energy X-ray projection image (or higher energy image). An energy subtraction X-ray image is produced by using the lower energy image dataset L(i,j) and the higher energy image dataset H(i,j).

A conventional data processing of the energy subtraction imaging can be performed by the data processing apparatus 400 shown in FIG. 2. The lower energy dataset L(i,j) stored in the storage device 311 of the imaging device 310 is transmitted to the data processing apparatus 400 through the process unit of the imaging device 310. The higher energy dataset H(i,j) stored in the storage device 311 of the imaging device 330 is transmitted to the data processing apparatus 400 through the process unit of the imaging device 330.

As an example, an energy subtraction data processing may be written as follows.

$$D(i,j)=|\alpha_1 L(i,j)-\alpha_2 H(i,j)|+\alpha_3 \quad (1)$$

where $D(i,j)$ is an energy subtraction image dataset, $H(i,j)$ is the higher energy image dataset, $L(i,j)$ is the lower energy image data, $\alpha_1$ and $\alpha_2$ are weighting factors and $\alpha_3$ is a display offset factor for enhancing quality of displaying an energy subtraction image. $\alpha_1$ and $\alpha_2$ are relevant to X-ray doses received by the imaging device 310 and the imaging device 330 respectively. Also, $\alpha_1$ and $\alpha_2$ are appropriately chosen to form either a bone dominated image or a soft-tissue image. For example, in order to obtain a soft-tissue image (a bone eliminated image), $\alpha_1$ and $\alpha_2$ may be chosen to satisfy $\alpha_1 L(i,j) > \alpha_2 H(i,j)$. Further, in order to obtain a soft tissue eliminated image (bone image) is produced, $\alpha_1$ and $\alpha_2$ may be chosen to satisfy $\alpha_1 L(i,j) < \alpha_2 H(i,j)$.

The energy subtraction data processing for producing the energy subtraction image dataset $D(i,j)$ can be performed frame image by frame image using the lower energy image dataset $L(i,j)$ and the higher energy image dataset $H(i,j)$. The X-ray imaging apparatus 300 is configured to obtain the lower energy image dataset $L(i,j)$ and the higher energy image dataset $H(i,j)$ while the X-rays 101 are being emitted from the X-ray source 100. The energy subtraction image data $D(i,j)$, the lower energy image dataset $L(i,j)$ and the higher energy image dataset $H(i,j)$ indicate digital grayscale. When necessary, the energy subtraction data processing may be selectively performed at a predetermined area of the X-ray imaging apparatus 300. For example, either a soft-tissue image (bone eliminated image) or a bone image can be formed at a specific part of the object 200 with a standard X-ray image or an opposite image, in which the opposite image of the soft-tissue image is the bone image and the opposite image of the bone image is the soft-tissue image.

In a specific application, the radiation of the X-rays 101 emitted by the X-ray source 100 may be a continuous exposure to the object 200 for monitoring and recording motion X-ray images for a predetermined time period (during operations of the X-ray source), depending upon its application. In this case, real-time energy subtraction X-ray imaging can be performed by reading the energy subtraction image dataset $D(i,j)$ produced by the data processing apparatus 400 while the X-rays 101 are emitted from the X-ray source 100 and outputting the energy subtraction dataset $D(i,j)$ through a display monitor of the computer unit 500. In another example, another display monitor may be connected to perform the energy subtraction imaging with the display monitor.

According to another embodiment of the present invention, the data processing apparatus 400 may perform the energy subtraction image for a specific area (a predetermined area) of interest of the pixel arrays 315 of the image device 310 and 330 of the X-ray imaging apparatus 300. This allows an operator to show partial energy subtraction data processing, in which a bone eliminated image of interest surrounding a soft tissue eliminated image can be complementary shown in a single frame image in real time. In another case, a soft tissue eliminated image of interest surrounding a bone image or a conventional X-ray image or other combinations can be complementary shown in a single frame image in real time. Further, any of the energy subtraction images can be formed as a static single frame image.

In accordance with an embodiment of the present invention, each storage device 313 of the imaging device 310 and 330 may include information of noise correction data (predetermined offset noise data).

Noise of the X-ray imaging apparatus 300 is caused by parasitic capacitance distributed along the TFTs 48 and non-uniformity of the signal generating layer 42 or electrodes of each of the imaging devices 310 and 330. When receiving the X-rays, each noise level of images produced by the imaging devices 310 and 330 is proportional to the exposure of detective pixels to radiation of the X-rays 101.

Figure 7:
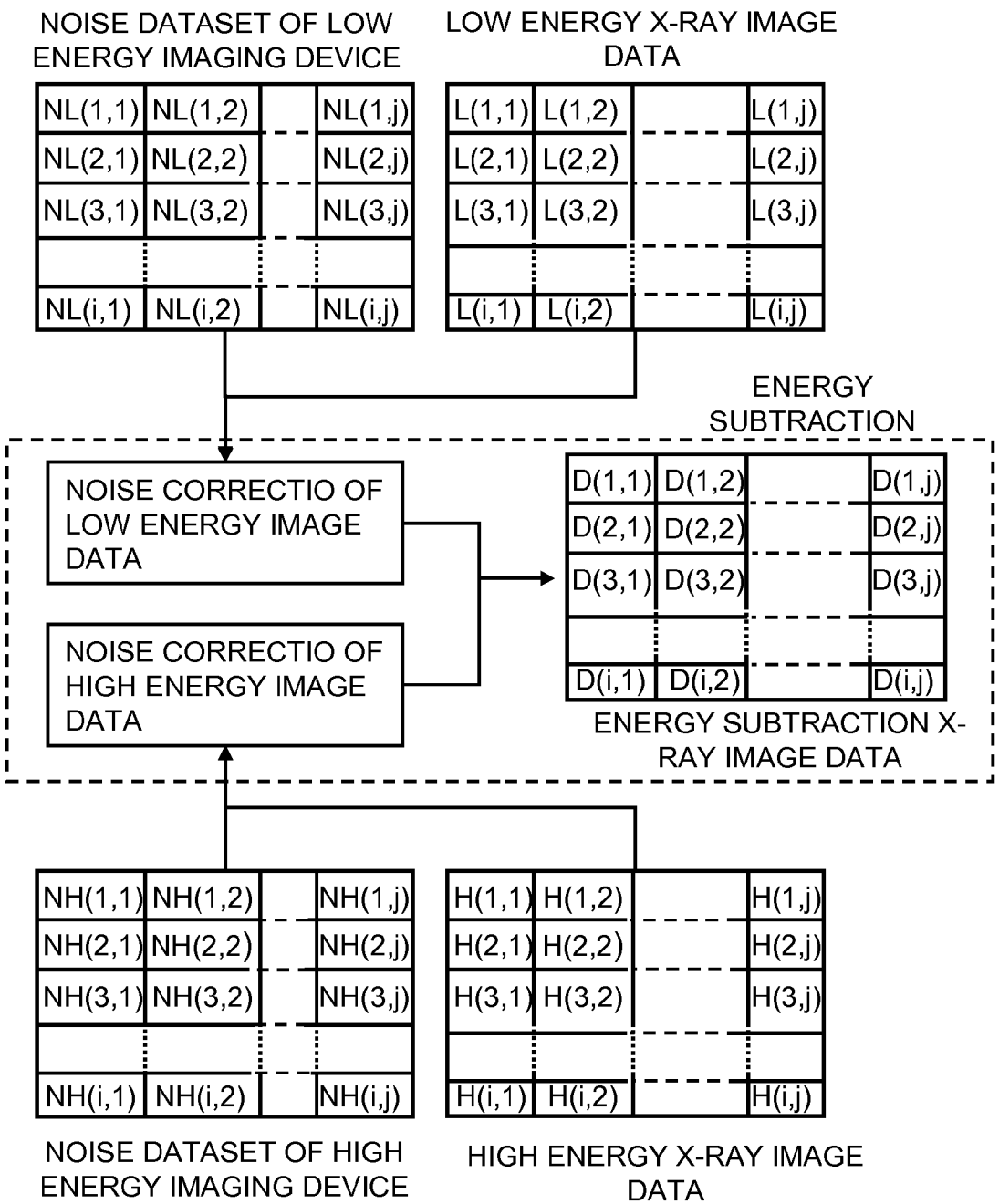
FIG. 7 illustrates an embodiment of dataset structures including noise correction datasets for producing an energy subtraction X-ray image dataset.

FIG. 7 illustrates another embodiment of dataset structures including noise correction datasets (predetermined offset noise datasets) for producing an energy subtraction X-ray image dataset. Noise levels of the detective pixel 311 of the imaging devices 310 and 330 are written as NL(i,j) and NH(i, j), respectively. The noise levels of imaging devices 310 and 330 can be minimized by eliminating individual noises of the imaging devices 310 and 330. In a way of minimizing the noise levels of the imaging devices 310 and 330, a noise dataset NL(i,j) and a noise dataset NH(i,j) are included in the X-ray imaging apparatus 300. The noise datasets NL(i,j) and NH(i,j) may be stored in the process unit (not shown) of the data processing apparatus 400. Alternatively, the noise datasets NL(i,j) and NH(i,j) may be included in each of the storage devices 313 of the imaging devices 310 and 330. Further, the noise datasets NL(i,j) and NH(i,j) may be included in the computer unit 500. The noise dataset NL(i,j) corresponds to the lower X-ray image dataset L(i,j) of the imaging device 310, and the noise dataset NH(i,j) corresponds to the higher X-ray image dataset H(i,j) of the imaging device 330. As an example, another energy subtraction data processing may be written as follows.

$$D(i,j)=|b_1[L(i,j)-NL(i,j)]-b_2[H(i,j)-NH(i,j)]|+b_3 \quad (2)$$

where D(i,j) is an energy subtraction image dataset, H(i,j) is the higher energy image dataset, L(i,j) is the lower energy image data, $b_1$ and $b_2$ are weighting factors and $b_3$ is a display offset factor for enhancing quality of displaying an energy subtraction image. $b_1$ and $b_2$ are relevant to doses received by the imaging device 310 and the imaging device 330 respectively. Also, $b_1$ and $b_2$ are appropriately chosen to form either a bone dominated image or a soft-tissue image. For example, in order to obtain a soft-tissue image (a bone eliminated image), $b_1$ and $b_2$ may be chosen to satisfy $b_1[L(i,j)-NL(i,j)] > b_2[H(i,j)-NH(i,j)]$. Further, in order to obtain a soft tissue eliminated image is produced, $b_1$ and $b_2$ may be chosen to satisfy $b_1[L(i,j)-NL(i,j)] < b_2[H(i,j)-NH(i,j)]$.

The noise datasets NL(i,j) and NH(i,j) are obtained by radiation of the X-rays 101 onto the X-ray imaging apparatus 300 without the object 200. The dose of the X-rays 101 for obtaining the noise datasets NL(i,j) and NH(i,j) may be appropriately adjusted by controlling the X-ray source 100 by the X-ray source control unit 110. The noise datasets NL(i,j) and NH(i,j) indicate digital grayscale.

For another example of the X-ray imaging apparatus 300, only single storage device 313 may be included in the X-ray imaging apparatus 300, and the noise datasets NL(i,j) and NH(i,j) may be included in that single storage device 313 of the X-ray imaging apparatus 300. The single storage device 313 may be disposed separately from the imaging devices 310 and 330. Therefore, at least one storage device 313 is included in the X-ray imaging apparatus 300. Further, in some cases, either one of the noise dataset NL(i,j) or the noise dataset NH(i,j) may be used in in equation (2). When only the noise dataset NL(i,j) is used, the noise dataset NH(i,j) may be set to zero. When only the noise dataset NH(i,j) is used in equation (2), the noise dataset NL(i,j) may be set to zero.

Figure 8:
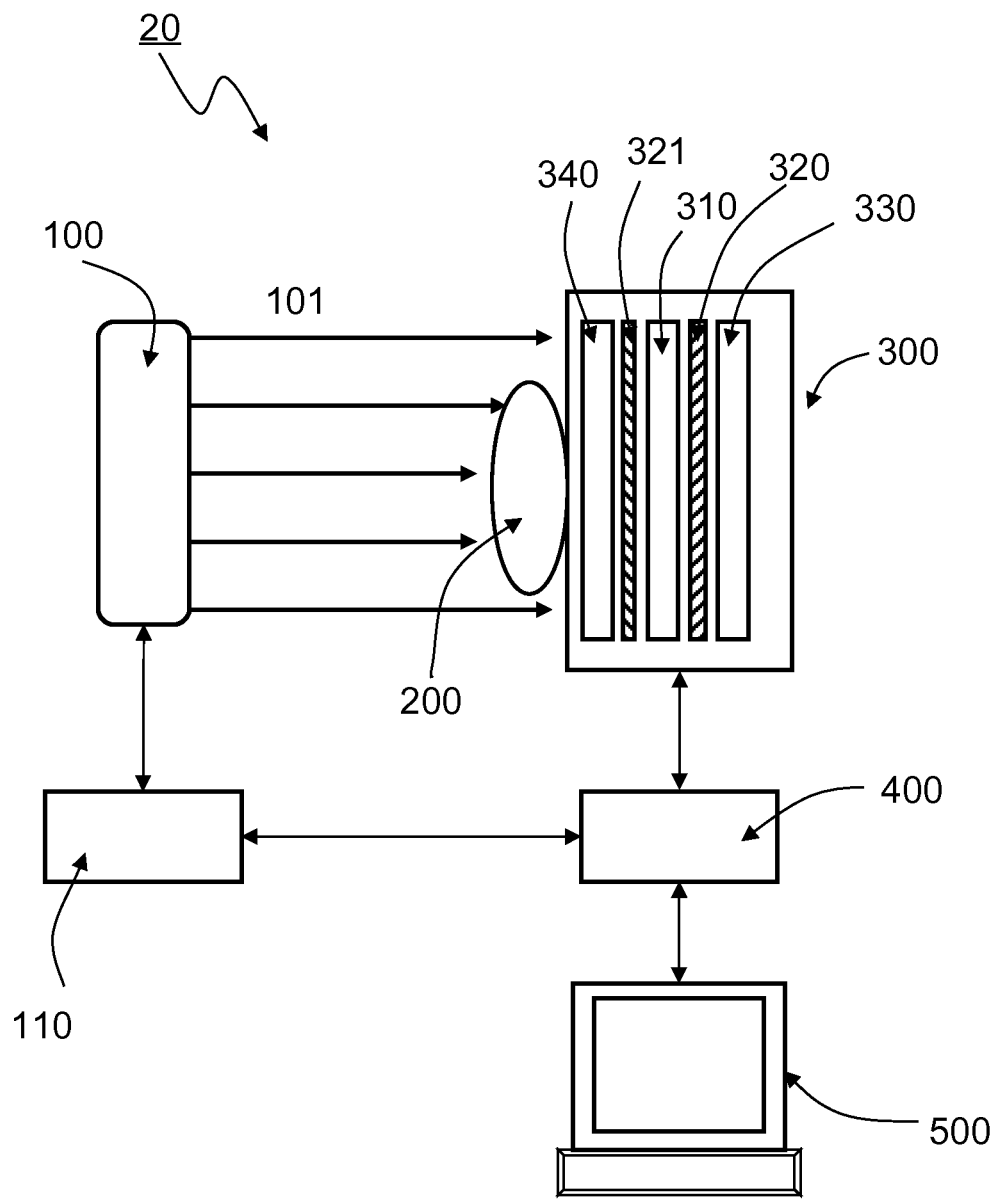
FIG. 8 illustrates another embodiment of an energy subtraction imaging system.

FIG. 8 shows an illustration of another energy subtraction imaging system 20 in accordance with an embodiment of the present invention. In FIG. 8, identical notations are used with reference to parts that are used in FIG. 1 and explanation of the identical parts is omitted.

The X-ray imaging apparatus 300 includes a front imaging device 340, a front attenuating element 321, the imaging device 310, the attenuating element 320 and the imaging device 330. The front attenuating element 321 is configured to substantially absorb the X-rays 101 at lower energy levels around between 35 keV and 60 keV, more specifically between 40 keV and 50 keV. Therefore, the front imaging device 340 and the imaging device 310 receive the X-rays 101 at lower energy. This make it possible for the front imaging device 340 and the imaging device 310 to produce energy subtraction images that show substantially different contrast for soft-tissue and fat of the object 200, because attenuation coefficients of the soft-tissue and fat are reasonably different for the X-rays 101 at energy levels between 35 keV and 60 keV. The front attenuating element 321 may be formed by a tin (Sn) film. For example, a thickness of the Sn film may be approximately between 0.5 mm and 1.5 mm, more specifically, between 0.7 mm and 1.0 mm. For the front attenuating element 321 may be formed from a material such as copper (Cu), molybdenum (Mo), cadmium (Cd), tellurium (Te), indium (In), silicon (Si), gallium arsenide (GaAs), gallium nitride (GaN), indium arsenide (InAs), indium antimonide (InSb), selenium (Se) or a material made from combination of those materials.

When X-ray image datasets formed by the front imaging device 340 and the imaging device 310 are written as FL(i,j) and L(i,j) respectively, a lower energy subtraction image dataset FD(i,j) may be described as follows.

$$FD(i,j)=|c_1FL(i,j)-c_2L(i,j)|+c_3 \quad (3)$$

where FD(i,j) is the lower energy subtraction image dataset, FL(i,j) is the front lower energy image dataset, L(i,j) is the lower energy image dataset, $c_1$ and $c_2$ are weighting factors and $c_3$ is a display offset factor for enhancing quality of displaying an energy subtraction image. $c_1$ and $c_2$ are relevant to X-ray doses received by the imaging device 340 and the imaging device 310 respectively. Also, $c_1$ and $c_2$ are appropriately chosen to form either a fat dominated image or a soft-tissue dominated image. For example, in order to obtain a fat image, $c_1$ and $c_2$ may be chosen to satisfy $c_1FL(i,j) > c_2L(i,j)$. Further, in order to obtain a soft tissue is produced, $c_1$ and $c_2$ may be chosen to satisfy $c_1FL(i,j) < c_2L(i,j)$.

The energy subtraction data processing for producing the lower energy subtraction image dataset FD(i,j) can be performed frame image by frame image using the front lower energy image dataset FL(i,j) and the lower energy image dataset D(i,j). The X-ray imaging apparatus 300 is configured to obtain the front lower energy image dataset FL(i,j) and the lower energy image dataset L(i,j) while the X-rays 101 are being emitted from the X-ray source 100. The lower energy subtraction image data FD(i,j), the front lower energy image dataset FL(i,j) and the lower energy image dataset L(i,j) indicate digital grayscale. When necessary, a lower energy subtraction data processing may be selectively performed at a predetermined area of the X-ray imaging apparatus 300. For example, either a fat image or a soft-tissue image can be formed at a specific part of the object 200 with a standard X-ray image, a bone image or an opposite image. The opposite image of the soft-tissue image is the fat image and the opposite image of the fat image is the soft-tissue image.

The size of the front imaging device and the imaging devices 340 and 330 may be chosen for imaging a larger object and the number of the columns and rows may be changed depending upon a specific purpose of an application.

A single storage device 313 may be used and included in the X-ray imaging apparatus 300. The storage device 313 may be positioned separating from the imaging devices 310 and 330 and the front imaging device 340.

It should be understood that various modifications of the above described embodiments can be made by those skilled in the art after reading the specification of the subject application. These modifications are within the scope of the present invention. For example, the detector array 311 in the X-ray imaging apparatus 300 may be replaced with charge detectors that are capable of performing the same functions described herein. Further, the X-ray imaging apparatus 300 is not limited to being used on an imaging system with an X-ray radiation source capable of generating X-rays at different energy levels. The X-ray imaging apparatus 300 can be used on different imaging systems, each system including an X-ray radiation source that is capable of generating X-ray radiation either at a single energy level or at multiple energy levels.

Thus, although several preferred embodiments have been shown and described, it would be apparent to those skilled in the art that many changes and modifications may be made thereunto without the departing from the scope of the invention, which is defined by the following claims and their equivalents.

Other objects, features and advantages of the present invention will become more apparent from the following detailed description when read in conjunction with the accompanying drawings.

What is claimed is:

1. An energy subtraction radiographic imaging system for providing energy subtraction images of an object, comprising:
    an X-ray radiation source configured to generate X-rays having various energy levels including lower energy levels and higher energy levels transmitting through the object;
    a radiation imaging apparatus configured to operate in association with operation of the X-ray radiation source for receiving X-rays transmitted through the object, the radiation imaging apparatus including a first imaging device, a second imaging device and an attenuating element disposed between said first imaging device and said second imaging device, the attenuating element configured to substantially absorb the X-rays at lower energy levels and substantially allowing transmission of the X-rays at higher energy levels so that said second imaging device substantially receives the X-rays at higher energy levels,
    said first imaging device configured to include a first pixel array generating first electric signals by receiving the X-rays transmitted through the object and include a first circuitry acquiring said first electric signals from said first pixel array and forming first digital image data of the object using said first electric signals for outputting said first digital image data, and a
first storage device for storing said first digital image data of the object output from the first circuitry,
    said second imaging device configured to include a second pixel array generating second electric signals by receiving the X-rays at higher energy levels transmitted through the attenuating element and include a second circuitry acquiring said second electric signals from the second pixel array and forming second digital image data of the object using said second electric signals output from the second circuitry, and a second storage device for storing said second digital image data of the object output from the second circuitry; and
    an image processing device configured to acquire said first and second digital image data output respectively from said first and second imaging devices for providing energy subtraction radiographic images of the object using said first and second digital image data.

2. The energy subtraction radiographic imaging system as claimed in claim 1, wherein at least one of the first and second storage devices configured to store predetermined offset noise data of the pixel array.

3. The energy subtraction radiographic imaging system as claimed in claim 1, wherein at least one storage device is included in the radiation imaging apparatus.

4. A radiation imaging apparatus for providing subtraction images of an object comprising:
    a first imaging device, a second imaging device and an attenuating element disposed between said first imaging device and said second imaging device, said first and second imaging device configured to receive X-rays at various energy levels including higher energy levels and lower energy levels, the attenuating element configured to substantially absorb the X-rays at the lower energy levels and substantially allowing transmission of the X-rays at the higher energy levels so that said second imaging device receives the X-rays at the higher energy levels, said first imaging device configured to include a first pixel array generating first electric signals by receiving the X-rays transmitted through the object and include a first circuitry acquiring and outputting said first electric signals, said second imaging device configured to include a second pixel array generating second electric signals by receiving the X-rays transmitted through the attenuating element and include a second circuitry acquiring and outputting said second electric signals; and
    an image processing device configured to acquire said first and second electric signals output from said first and second imaging devices for processing said first and second electric signals for providing subtraction radiographic images;
    wherein said first and second imaging devices operate in association with one another for processing characteristics of the X-rays.

5. The radiation imaging apparatus as claimed in claim 4, further comprising at least one storage device configured to store said first and second electric signals output from said first and second imaging devices.

6. The radiation imaging apparatus as claimed in claim 4, further comprising a third imaging device positioned so that the third imaging device receives the X-rays transmitted through the second imaging device.

7. The radiation imaging apparatus as claimed in claim 4, wherein the first imaging device is configured to substantially transmit the X-rays at higher energy levels.

8. The radiation imaging apparatus as claimed in claim 4, wherein the second imaging device is configured to substantially absorb the X-rays at higher energy levels.

9. The radiation imaging apparatus as claimed in claim 4, wherein the first imaging device and the second imaging device are configured to continually acquire and output the first and second electric signals so as to provide a real-time output to the image processing device.

10. The radiation imaging apparatus as claimed in claim 4, wherein the image processing device is configured to process the first and second electric signals in real-time so as to provide a digital motion image.

11. The radiation imaging apparatus as claimed in claim 4, further comprising a third imaging device and a second attenuating element positioned between said third imaging device and the first imaging device so that said third imaging device and the first imaging device receives the X-rays transmitted through the object.

12. The radiation imaging apparatus as claimed in claim 4, wherein the attenuating element is made from copper (Cu), molybdenum (Mo), cadmium (Cd), tin (Sn), silicon (Si), gallium arsenide (GaAs), gallium nitride (GaN), indium arsenide (InAs), indium antimonide (InSb), selenium (Se), tellurium (Te), indium (In) or a material made from combination of those materials.

13. The radiation imaging apparatus as claimed in claim 4, wherein the attenuating element is made from semiconductor.

14. The radiation imaging apparatus as claimed in claim 11, wherein said second attenuating element is made from made from copper (Cu), molybdenum (Mo), cadmium (Cd), tin (Sn), silicon (Si), gallium arsenide (GaAs), gallium nitride (GaN), indium arsenide (InAs), indium antimonide (InSb), selenium (Se), tellurium (Te), indium (In) or a material made from combination of those materials.

15. The radiation imaging apparatus as claimed in claim 11, wherein said another imaging device, said second attenuating element and the first imaging device are configured so as to detect the X-rays at the lower energy levels.

16. The radiation imaging apparatus as claimed in claim 4, wherein the image processing device provides the energy subtraction radiographic images for a predetermined area of the radiation imaging apparatus.

17. The radiation imaging apparatus as claimed in claim 4, wherein said at least one storage device is configured to store predetermined offset noise data.

18. A computer readable recording medium having instructions executable by a computer to execute an energy subtraction radiographic imaging method, the method comprising the steps of:
receiving X-rays at various energy levels including higher energy levels and lower energy levels using a first imaging device converting signals caused by the X-rays into a first digital image dataset;
receiving the X-rays using an attenuating element substantially absorbing the X-rays at lower energy levels and substantially transmitting the X-rays at higher energy levels;
receiving the X-rays at higher levels using a second imaging device converting signals caused by the X-rays at higher energy levels into a second digital image dataset; and
forming an energy subtraction image dataset using said first digital image dataset and second image dataset.

\* \* \* \* \*